(12) United States Patent
Goldenberg

(10) Patent No.: US 7,384,400 B2
(45) Date of Patent: *Jun. 10, 2008

(54) BONE MARROW BIOPSY NEEDLE

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 0 days.

This patent is subject to a terminal disclaimer.

(21) Appl. No.: 11/742,333

(22) Filed: Apr. 30, 2007

(65) Prior Publication Data

US 2007/0265548 A1 Nov. 15, 2007

Related U.S. Application Data

(63) Continuation-in-part of application No. 11/416,451, filed on May 1, 2006, now Pat. No. 7,338,456.

(51) Int. Cl.
*A61B 10/00* (2006.01)

(52) U.S. Cl. ....................................... 600/564

(58) Field of Classification Search ................ 600/564, 600/562, 566, 567, 568; 606/167, 170
See application file for complete search history.

(56) References Cited

U.S. PATENT DOCUMENTS

| | | | |
|---|---|---|---|
| 3,605,721 A | 9/1971 | Hallac | |
| 4,262,676 A | 4/1981 | Jamshidi | |
| 5,074,311 A | 12/1991 | Hasson | |
| 5,522,398 A | 6/1996 | Goldenberg et al. | |
| 5,634,473 A | 6/1997 | Goldenberg et al. | |
| 6,015,391 A | 1/2000 | Rishton et al. | |
| 6,471,709 B1 | 10/2002 | Fawzi et al. | |
| 2005/0054948 A1* | 3/2005 | Goldenberg | ................ 600/567 |

* cited by examiner

*Primary Examiner*—Max Hindenburg
*Assistant Examiner*—Emily M Lloyd
(74) *Attorney, Agent, or Firm*—Leason Ellis LLP

(57) ABSTRACT

A biopsy needle for removal of tissue from a patient includes an outer tube having a distal end that has an inner diameter (IDtip) and an inner tube within the outer tube and having an inner diameter (IDsc), defined at the distalmost section of the inner tube. The needle also includes a snare having a first end connected to the inner tube and a second end coupled to the outer tube. The snare has a variable diameter that is controlled by rotation of the inner tube with respect to the outer tube in a prescribed direction resulting in the opening and closing, respectively, of the snare. A ratio (R) defined as (IDsc)/(IDtip) is greater than 1.

18 Claims, 5 Drawing Sheets

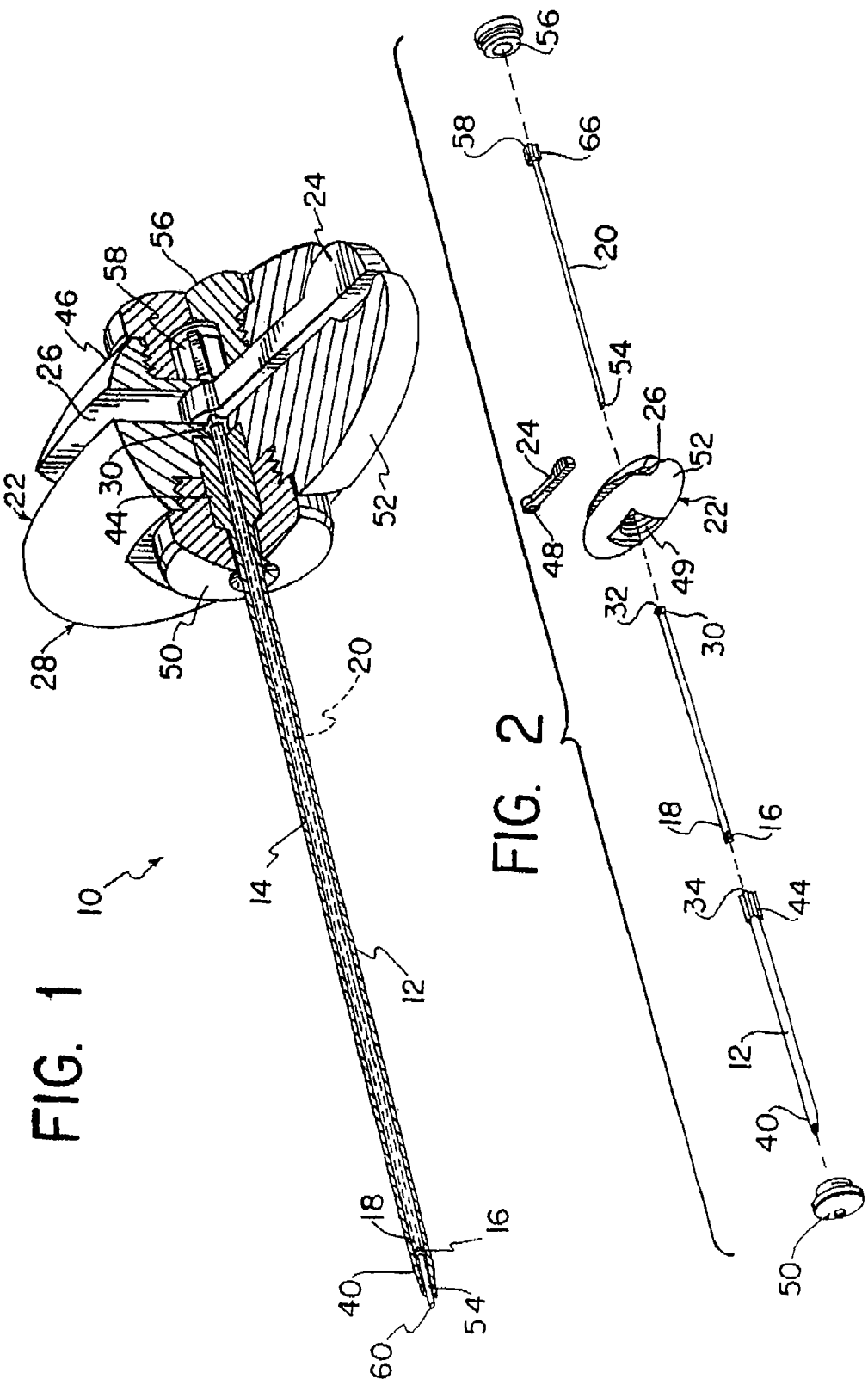

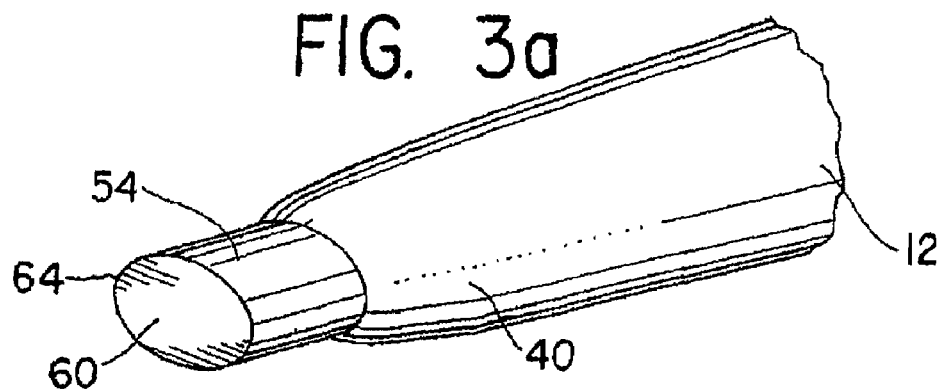
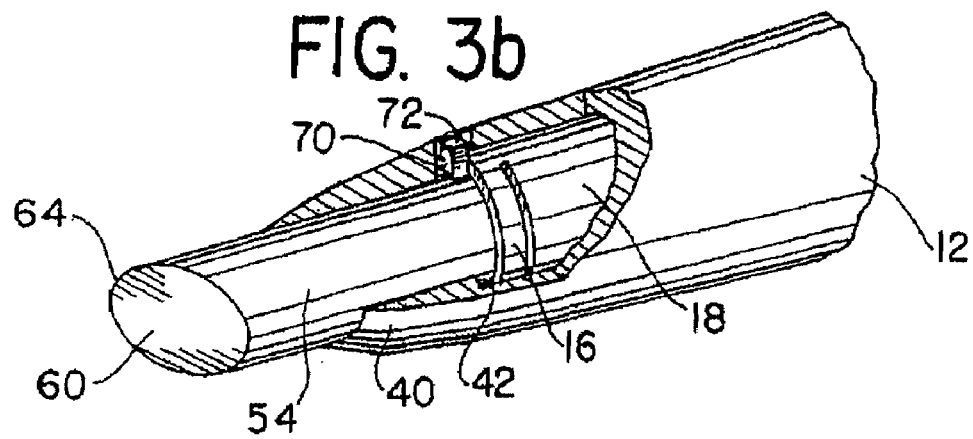
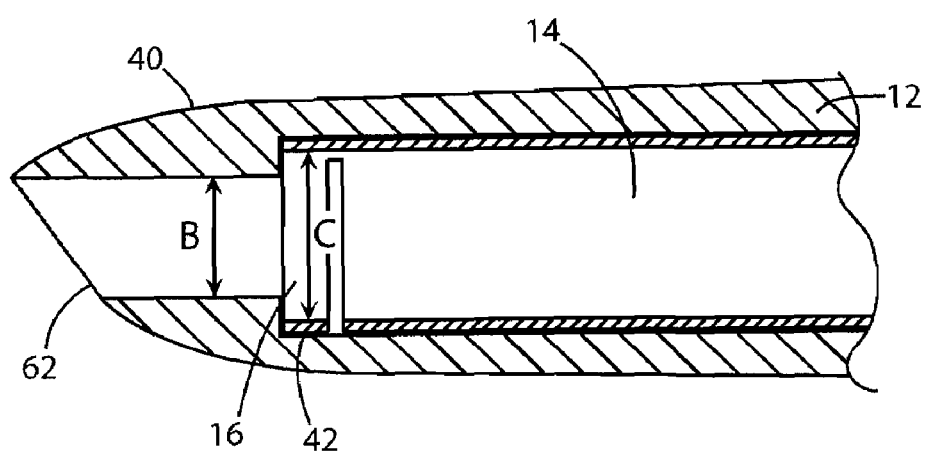

BONE MARROW BIOPSY NEEDLE

CROSS-REFERENCE TO RELATED APPLICATION

The present application is a continuation-in-part of U.S. patent application Ser. No. 11/416,451, filed May 1, 2006, which is hereby incorporated by reference in its entirety.

TECHNICAL FIELD

This invention relates generally to a surgical instrument, known variously as a biopsy needle or cannula that is used to gather tissue, such as bone marrow, from living persons or animals for pathological study. More specifically, the invention relates to a biopsy needle having an improved structure for severing a tissue sample and/or retaining the tissue sample within the needle.

BACKGROUND

For various medical reasons, such as evaluating the histology and/or pathology of a tissue, it is often necessary for a physician to obtain a sample of a patient's body tissue. In particular, bone marrow is frequently retrieved to study its cellularity and potential infiltration with abnormal cells. The currently available procedures and instruments used for obtaining bone marrow biopsy samples, while not overly complex, almost universally result in excessive patient discomfort and often recover inadequate quantities of biopsy material which sometimes is distorted and/or difficult to interpret. In the standard bone marrow procurement protocol, using currently available instruments, (such as those disclosed in U.S. Pat. No. 4,262,676 to Khosrow Jamshidi), the patient is prepared with a suitable local anesthetic at the posterior superior iliac crest/spine. Then, a relatively narrow needle is inserted to obtain an aspirate of liquid bone marrow material to make slides for examination of cellular morphology and to evaluate the surface immunophenotype of the bone marrow cells with flow cytometry. This portion of the procedure, referred to as the bone marrow aspiration, is generally relatively less painful than the bone marrow biopsy procedure using a conventional biopsy needle. Using newer bone marrow biopsy needles which actively capture specimens, and minimize manipulation of the needle after insertion, the aspirate procedure appears to be more painful than the biopsy procedure.

After the aspirate is obtained, if necessary, a biopsy of the bone marrow is taken. A significantly wider bore needle having an inner diameter that will accommodate a suitable marrow sample is prepared with an inner stylet that extends beyond the distal end of the outer needle. The stylet's distal end may be cut at an angle, with the leading edge sufficiently sharp to pierce tissue and bone. With the stylet in place within the outer needle, the needle is pushed through the outer layers of skin and subcutaneous tissue until the needle tip reaches the surface of the cortical bone. The needle and stylet are then pushed into and through the cortical layer until the tip has penetrated into the bone marrow space.

The stylet is then removed from the proximal end of the needle, which opens up the core of the needle to accommodate entry of bone marrow material for collection and retrieval. The needle is then usually advanced another 1 to 2 centimeters at minimum with a slight twisting motion. Often, the distal end of the needle will also be provided with an angled cut and sharpened leading edge to facilitate cutting and coring the tissue. By providing a slight twisting motion as the needle is advanced, usually with no more than quarter or half turns, an appropriate sample is cored from the marrow tissue and enters the inner passage of the marrow needle.

At this point, the marrow biopsy sample is ready to be removed from the patient, although it is important that the biopsy remain within the needle as the needle is withdrawn to ensure recovery of the specimen. If the biopsy becomes dislodged and falls through the distal end of the biopsy needle, the specimen is irretrievably lost. The procedure is then unsuccessful and must be repeated from the beginning.

Various methods have been utilized by physicians to try to prevent the biopsy specimen from dislodging from the needle. For example, after the needle has entered the bone and fully cored a sample from the marrow, some physicians will pull the biopsy needle back a few millimeters and then advance it a few millimeters at a different angle than the first insertion. This theoretically will "cut" the biopsy piece at the tip of the needle. Other physicians attempt to dislodge or disrupt the connection between the specimen and the bone by making multiple complete clockwise and counterclockwise rotations of the biopsy needle while within the bone. Some physicians even hit the proximal end of the biopsy needle at its handle in an attempt to mechanically disrupt the connection between the specimen and the additional bone.

As can be plainly realized, these manipulations at the end of the procedure, attempts at ensuring that the specimen remains within the needle, can often produce substantial discomfort and anxiety to the patient. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy, since the bone marrow itself is reinforced by the surrounding tissue. In those cases, the cored biopsy often remains attached to the bone and is not successfully recovered.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by deformation during the twisting process. Another disadvantage is the lack of control over the twisting motions or the breakage of the strips. Essentially, the operator is left to twist the inner tube until resistance to that twisting is lost, indicating that the strips have severed. There is also no way of releasing the device's grip on tissue during the procedure, should any problems arise.

U.S. Pat. No. 5,074,311 to Hasson discloses a biopsy device that includes a pair of inner jaws that can be actuated within the outer needle to "bite off" any biopsy piece that has entered the needle. The disadvantages of this device include multiple small mechanical linkages and parts including pivot pins, which are extremely difficult and expensive to assemble and maintain, in addition to the greatly increased chance of mechanical failure resulting in failure to retrieve an adequate specimen.

U.S. Pat. No. 5,522,398, to Goldenberg et al., discloses a bone marrow biopsy needle; however, the patent teaches that an inner diameter B at the distal tip of the needle (as shown in FIG. 4 thereof) is substantially equal to an inner diameter C of the inner tube (as shown in FIG. 3C) so that there will be no ridge or lip within the instrument to impede tissue entering the inner lumen of the needle. However, observations over time of the performance of needles constructed in this manner indicates that such a relationship may impede specimen transit into and through the needle, and that a virtual obstruction phenomena may develop as a result of the above relationship between the two inner diameters. Compromise of specimen transit into the needle results in an inability of the specimen to move forward into the lumen of the needle. In addition, as the needle penetrates tissue, external pressures, especially those produced by dense bone, could deform or change the diameter at the needle tip (inner diameter B) or might transmit a force through the wall of the needle, marginally decreasing the diameter of the inner tube or snare (inner diameter C). These changes could dynamically alter the relationship between the inner diameters and cause a virtual obstruction, impeding specimen transit and making it difficult for the specimen to move forward into the needle.

SUMMARY

According to the one aspect of the invention, an improved biopsy needle has an outer cannula, an inner tube and a stylet. The distal end of the inner tube is provided with a snare in the form of a coil extending from the inner tube. The free end of the coil is adhered to the outer cannula. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

In yet another aspect, a biopsy needle for removal of tissue from a patient includes an outer tube having a distal end, contributing to a needle tip, that has an inner diameter ($ID_{tip}$) and an inner tube within said outer tube. The needle also includes a snare having a first proximal end connected to the inner tube and having an inner distal diameter ($ID_{sc}$) and a second distal end coupled to the outer tube. The snare has a variable diameter that is controlled by rotation of the inner tube with respect to the outer tube in a prescribed direction resulting in the opening and closing, respectively, of the snare, wherein a ratio $(R)=(ID_{sc})/(ID_{tip})$ is greater than 1.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which:

FIG. 1 is a perspective view of a biopsy needle in accordance with the present invention;

FIG. 2 is an exploded view of the biopsy needle according to the present invention;

FIGS. 3a-3e are detail perspective views of the distal ends of various components during operation of the biopsy needle;

DETAILED DESCRIPTION OF THE PREFERRED EMBODIMENTS

Figure 3D:
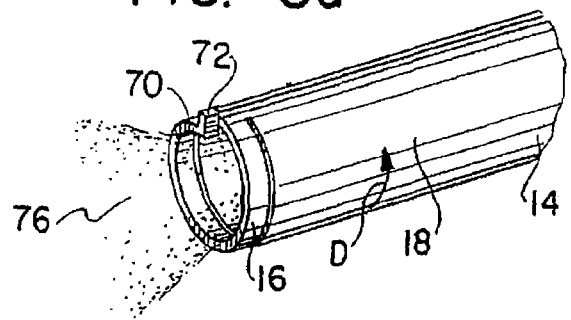

Referring now to FIGS. 1 and 2, a biopsy needle 10 has an outer cannula 12, an inner tube 14 with a snare 16 at its distal end 18, a stylet 20, and a handle assembly 22. In FIG. 2, the assembly of the present biopsy needle 10 is shown in an exploded view.

As part of the handle assembly 22, a lever 24 fits into a corresponding groove 26 within a handle piece 28. The lever 24 actuates the snare 16 within the outer cannula 12 without any movement of the outer cannula 12 relative to the patient (not shown). The functioning of this lever 24 is described more fully below. The inner tube 14 has a snare 16 at its distal end 18 and a gear or lever connector 30 mounted on its proximal end 32. The inner tube 14 is inserted into the proximal end 34 of the outer cannula 12 with the gear or lever connector 30 extending out of the proximal end 34, which facilitates connection of the lever to the inner tube and uniform conversion of lever rotation to inner tube rotation.

Figure 4:
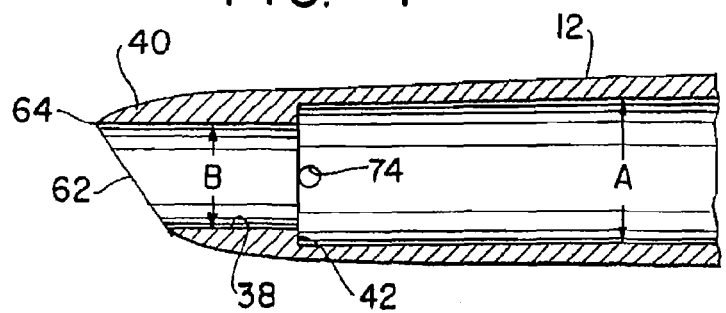
FIG. 4 is a cross-section of the distal end of the outer cannula.

As can be seen in FIG. 4, the interior of the outer cannula 12 has a constant inner diameter A along a majority of its length, and a portion 38 having a smaller inner diameter B at its distal tip 40 allowing the inner tube to fit within the outer tube while keeping the inner diameter of the inner tube C nearly equivalent to the inner diameter of the distal tip B.

In contrast to the teachings of the present inventor's prior '398 patent, the present applicant has discovered that the narrow inner diameter B at the distal tip 40 should not be substantially equal to the inner diameter C of the inner tube 14 in order to optimize the ability of the specimen to move forward into the needle. As described above, in the '398 patent design, there is specimen transit issue in that even though the distal tip inner diameter of the outer cannula is substantially equal to the snare coil inner diameter, the thickness of the snare coil creates an obstruction to entry of the specimen into the snare coil prior to wind down. This results in peripheral edges of the specimen encountering an obstruction prior to entry into the snare and consequently, the specimen can be damaged in an attempt to introduce it into the snare itself due to the obstruction.

The ability of the specimen to move forward into the needle 10 can be described by the following equation: $ID_{sc}(d)/ID_{tip}(d) \leq R$, where d is the needle penetration distance, $ID_{sc}(d)$ is the internal diameter of the most distal aspect of the snare (as indicated by the variable C in FIG. 3c) as a variable dependent on the penetration of the needle 10 into a tissue, and $ID_{tip}(d)$ is the internal diameter of the tip 40 which also may be dependent on forces that develop relative to the penetration of the needle a certain distance (d) into a tissue. In accordance with the present invention, the present applicant has discovered that R should be greater than one since as R increased, the potential interaction between the core specimen and the internal diameter (C) of the snare 16/inner tube 14 decreases. The internal diameters are described as variables dependent on the needle penetration distance (d), since it is possible, depending upon the structural integrity of the wall components, that external forces applied as the needle penetrates tissue could influence the specified internal diameters.

In accordance with the present invention, there is a direct correlation between needle performance and the R averages and the ratio R provides a valid descriptor of intraluminal specimen transit and needle performance. According to a first embodiment R>1.00; according to a second embodiment, R≧1.15; according to a third embodiment, R≧1.20; according to a fourth embodiment, R≧1.25; according to a fifth embodiment, R≧1.30; and according to a sixth embodiment, R≧1.35. It will be appreciated that the above values are merely exemplary in nature and that other values are equally suitable so long as the ratio R eliminates the occurrence of the obstruction phenomena that makes it difficult for the specimen to move forward into the needle 10 or compromises specimen recovery at the conclusion of the procedure. In one embodiment, R is greater than 1 and the snare is not at the distal end of the outer cannula but instead is spaced interiorly slightly from the distal end.

It will also be appreciated that since R represents a ratio, small differences in the values of the numerator and denominator can result in substantial practical and physical implications influencing specimen transit and needle performance. The applicant has therefore discovered that an R average value of about 1.0 or less will produce a virtual obstruction, which is not desirable during the specimen capture and withdrawal procedure. This is in direct contrast to Applicant's previous patent where diameter equivalence between the distal tip 40 and the inner tube 14 was suggested and still consistent with the concept of avoiding a ridge or lip between the distal tip 40 and the inner tube 14 which could impede tissue entering the instrument.

The inner tube 14 is inserted until the snare 16 reaches the shoulder 42 provided on the interior of the outer cannula 12 at the position where the diameter changes. However, other embodiments not requiring a shoulder are possible in which the outer surface of the inner tube is opposed to the inner surface of the outer tube, the two surfaces are bonded and the distal portion of the inner and outer tube are formed into a distal cutting tip.

With the gear or connector 30 extending proximal of the outer cannulats anchor 44, the cannula and snare assembly are attached to the handle piece 28 at the distal facing side 52 of the handle 22. The gear 30 of the inner tube 14 is inserted into a complementary hole 48 in the lever while the anchor 44 of the outer cannula 12 mates with a complementary hole 49 in the handle piece 28. Thus, when the lever 24 is rotated within its groove 26 with respect to the handle piece 28, the inner tube 14 will rotate with respect to the outer cannula 12. A cannula cap 50 is assembled onto the distal tip 40 of the cannula and threadedly engaged to the forward facing end of the handle piece 28. In other embodiments, a non-threaded cannula cap or similar retaining member can be bonded to the forward facing end of the handle piece 28 to ensure that the outer cannula 12 does not rotate or move longitudinally relative to the handle 28. The stylet 20 is inserted into the proximal end 32 of the inner tube until a distal tip portion 54 of the stylet extends beyond the distal tip 40 of the cannula. A stylet cap 56 can then be threadedly engaged to the proximal facing side 46 of the handle piece, covering the proximal end 58 of the stylet to prevent it from moving proximally within the inner tube 14. Other embodiments not requiring a stylet cap in which the proximal end of the stylet reversibly connects to the handle to prevent it from moving proximally are possible.

As can be seen in FIGS. 3a and 4, both the distal ends 40, 54 of the stylet and the outer cannula preferably have sloped end faces 60, 62 although it is not necessary. This improves the cutting actions of the both the stylet and the outer cannula by providing sharp leading edges 64. In this position, the stop 66 at the proximal end 58 of the stylet preferably mates with a complementary indent 68 (FIG. 7) in the handle piece 28 to maintain the rotational orientation of the stylet 20 with respect to the outer cannula 12 such that the slopes of the two distal ends 40, 54 are approximately parallel, or aligned optimally to result in an efficient piercing and cutting action and the stylet does not rotate relative to the outer cannula during the initial bone penetration. This is the configuration that would be used for initiating insertion of the biopsy needle 10 into the bony cortex.

As can be seen in FIG. 3b, which is a partial cutaway view, the free end 70 of the coil snare 16 includes a tab 72 that engages or is attached to a hole 74 (FIG. 4) on the interior surface of the outer cannula 12. This hole 74 preferably extends through the entire wall of the outer cannula. If desired, the tab 72 can be adhered to the hole 74 in the outer cannula through the use of adhesives, welding, or any known attachment process. However, it will be appreciated that the tab 72 and hole 74 can be eliminated and the outer surface of the inner tube can be bonded to the inner surface of the outer tube by welding or some other type of attachment method. It will therefore be appreciated that so long as the two structures are attached to one another, any number of different techniques can be used to accomplish such a coupling action, including the illustrated manner or using a direct bond between two surfaces, etc.

After the needle 10 is inserted into the marrow, the stylet 20 is removed proximally without any movement of the outer cannula 12 with respect to the patient, minimizing discomfort. As can be seen in FIG. 3c, marrow tissue may now enter the passageway within the outer cannula 12 through the distal end 40 of the outer cannula as the needle is advanced further and can enter the inner passageway of the inner tube 14, preferably to a position proximal of the snare 16.

Specimen transit refers to the process of specimen movement from the distal tip of the needle into the snare and inner tube lumen. The efficacy of specimen transit is modulated by the configuration of the tip and the relationship of $(ID_{sc})$ to $(ID_{tip})$. The advantages of snare capturing mechanisms are realized only by ensuring that specimen transit is maximized, according to the R value relationship.

Figure 3E:
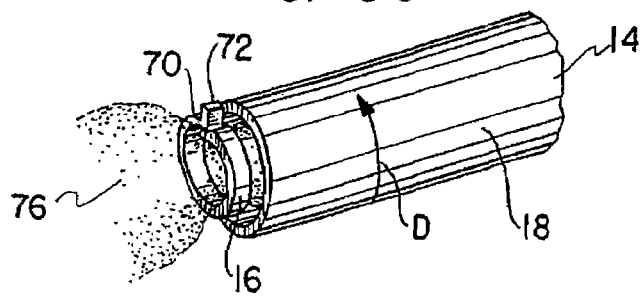
Figure 5:
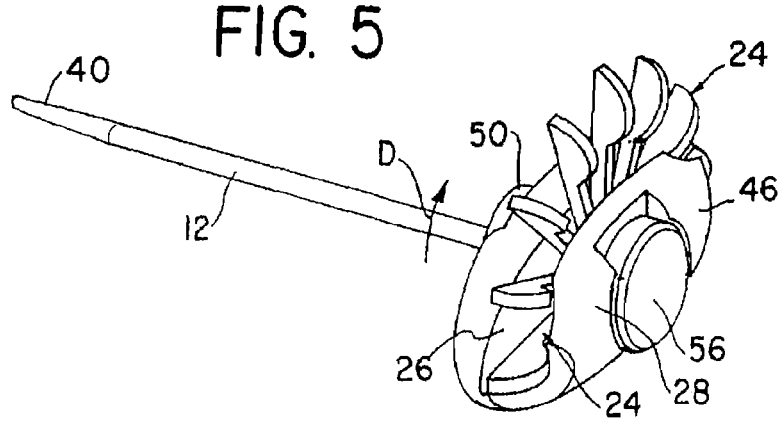
FIG. 5 is a perspective view of the biopsy needle showing operation by a physician.

To operate the snare 16, i.e. to cause cutting and/or holding of the biopsy piece 76 within the inner tube 14, the lever 24 attached to the proximal end 32 of the inner tube is rotated in the direction of arrow D as seen in FIGS. 3d-3e and 5. Of course, the snare 16 can be designed such that rotation in the opposite direction causes the same effect. With full rotation (180 degrees) of the lever 24, the inner tube 14 and snare 16 achieve a position similar to that shown in FIG. 3e, in which the inner tube 14 has been rotated approximately 180 degrees. Since the free end 70 of the snare is fixed to the outer cannula 12, the result of the rotation is that the coil of the snare 16 will tighten so that the cross-sectional area through the snare 16 is approximately less than a third of the area when in the open configuration. It is also contemplated that any decrease, even a slight decrease, in the cross-sectional area of the snare will cause pressure on the biopsy piece 76. Therefore, while the current amount of rotation is preferred, it is not necessary for the proper functioning of the present invention.

As seen in FIG. 5, movement of the lever 24 can be independent of any movement of the handle piece 28 or the outer cannula 12. Therefore, the outer cannula 12, which is in direct contact with the patient while the sample is taken, can remain substantially stationary. As motion of the outer cannula 12 relative to the patient, a painful maneuver, is not required to sever and capture the specimen, incorporation of the snare mechanism limits painful needle manipulations.

With the tightening of the snare 16, there is a high probability that the biopsy piece 76 will remain in the needle 10 and will be recovered as the needle is removed so long as efficient specimen transit has facilitated the passage of the specimen into the lumen of the snare and the inner tube. If the tightening of the snare 16 does not immediately cause the biopsy piece 76 to be cut, it will be significantly squeezed and/or notched, such that rearward motion of the needle 10, which causes rearward pressure on any biopsy piece 76 proximal of the snare 16, will cause material proximal of the snare 16 to detach from material that is distal of the snare.

Figure 7:
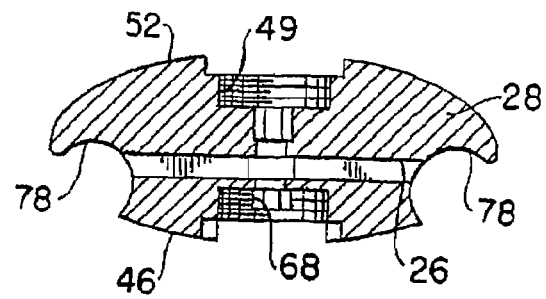
FIG. 7 is a cross-section view through the handle piece of the biopsy needle.

As can be seen in FIG. 7, the handle 22 includes several features designed for ease of use of the physician and ease of manufacture and construction. The handle piece 28 includes a groove 26 that holds the lever 24. The groove 26 has two notches 78 that generally protect the lever 24 from any accidental contact with the physician when in either the full-open or full-closed positions, but allow access to the lever. Further, the holes in the handle piece 28 that receive the anchor 44 of the outer cannula and the stop 66 of the stylet have complementary shapes in order to prevent rotation of those two components with respect to the handle, as previously discussed. The proximal and distal facing sides 46, 52 of the handle piece are also provided with threaded regions for receiving the cannula and stylet caps 50, 56.

Once the biopsy needle 10 has captured a cored specimen, it must be recovered for pathologic interpretation. The lever is rotated opposite to the direction D, thereby opening up the coil to its original diameter. An obturator is placed through the tip of the needle and the specimen is pushed through the inner tube and through the handle for collection. As initial efficient specimen transit into the inner tube influences transit of the specimen through the remainder of the inner cannula during the specimen recovery phase of the procedure, maximizing the R value also positively influences specimen recovery. Once the specimen has been ejected and recovered, the biopsy needle 10 is then ready to be sterilized for its next use. If necessary, the entire biopsy needle can be disassembled, although the tab 72 at the free end of the snare must be disengaged from the hole 74 in the outer cannula. This can be accomplished with any small tool pushed through hole 74. If the free end 70 of the snare is permanently adhered to the outer cannula 12, it then may be necessary to sterilize the outer cannula and inner tube as a single unit. However, due to the few number of parts and relative ease and low cost of construction of the present needle, it is also contemplated that such a device is easily disposable.

Figure 6A:
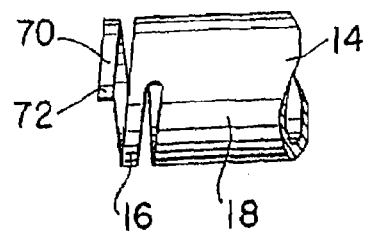
FIG. 6A is a detail side view of the inner tube of the present invention according to one embodiment.
Figure 6B:
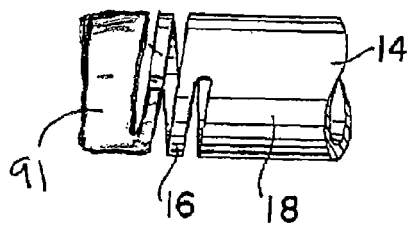
FIG. 6B is a detail side view of the inner tube of the present invention according to another embodiment.

FIG. 6b shows another embodiment where the snare 16 is not located at the distalmost section of the inner tube 14 but instead is spaced slightly inward from the distal end. A distal end section 91 is provided and in this embodiment (as mentioned above), the inner tube 14 is not attached to the outer tube via a tab and opening but instead, the inner tube 14 can be attached by means of the distal end section 91. It will be appreciated that the most distal inner diameter of the inner tube 14 at the most distal aspect of section 91, designated as $ID_{int}$, defines the ratio $R=(ID_{int})/(ID_{tip})$ When the most distal portion of the inner tube 14 is the most distal portion of the snare 16, the ratio is defined as $(ID_{sc})/(ID_{tip})$ since $ID_{sc}=ID_{int}$; however, when a small portion (section 91) of the inner tube 14 is distally located relative to the snare 16, the ratio R is $=(ID_{int})/(ID_{tip})$, where $(ID_{int})$ is the inner diameter of the most distal portion of the inner tube 14. It will be appreciated that the distal end section 91 can have a diameter that is different than the diameter of the adjacent snare 16.

Thus, it can be seen that a low cost, simply-manufactured biopsy needle will attain improved results over known devices, not only in the success rate of the marrow extraction procedures, but also a marked increase in patient comfort throughout the procedure. High performance needles require not only efficient specimen capture but efficient specimen transit through the needle. One desirable side benefit of this increased comfort might be increased participation in bone marrow donor programs for transplant candidates.

Figure 8:
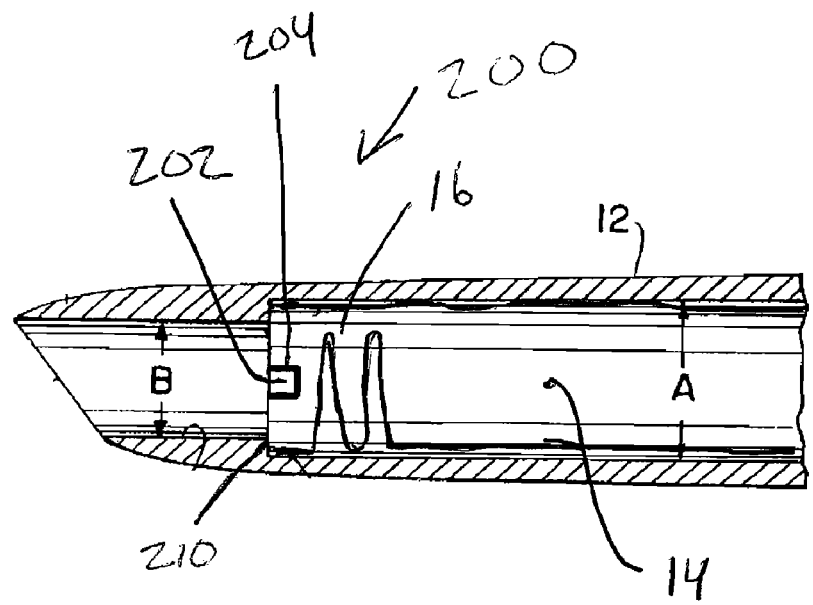
FIG. 8 is a cross-sectional view of a biopsy needle according to another embodiment.

Now referring to FIG. 8, a biopsy needle 200 is illustrated. In this design, the snare 16 engages the outer cannula 12, through corresponding axially directed coupling elements 202, 204 similar to the ones disclosed in Applicant's U.S. Pat. No. 6,015,391, which is hereby incorporated by reference in its entirety. At a distal end 210 of the snare 16, the coupling element 204 is formed and can be in the form of a notch. The notch 204 engages an axially directed tab or projection 202 that is associated with the outer cannula 12. For example, one or more tabs 202 can be provided along an inner surface of the outer cannula 12 near and interface where the reduced diameter portion of the outer cannula 12 transitions to the portion of the outer cannula 12 that has a greater diameter than the more distal section in order to accommodate the inner tube 14. When the tab 202 engages the notch 204, the snare 16 and the inner tube 14 are securely coupled to the outer cannula 12 so that rotation of the proximal end of the inner tube 14 causes the winding down (or opening up) of the snare 16.

The axially directed coupling members 202, 204 provide a simple biopsy structure for assembling and coupling the snare 16 and inner tube 14 to the cannula 12. It will also be appreciated that the arrangement of the coupling member 202, 204 preserves the R ratio described above and in particular, the distal end of the outer cannula 12 and the snare 16 are constructed so that the ratio R is greater than 1, thereby eliminating the occurrence of the obstruction phenomena that makes it difficult for the specimen to move forward into the needle 10 or compromises specimen recovery at the conclusion of the procedure. Thus, the shoulder formed between the reduced diameter distal end section of the outer cannula 12 and the greater diameter section acts as a stop to restrict further axial movement of the inner tube 14 toward the distal tip of the outer cannula 12. In addition, the projection 202 is formed in this region so that it engages notch 204 when the inner tube 14 abuts or is proximate the shoulder formed as part of the inner surface of the outer cannula 12.

It will be appreciated that the distal end 210 can include more than one notch 204 for engaging respective axial tabs 202 and it can be further appreciated that the notch and tab cooperate to retain the snare within the outer cannula. The snare is thus contained within the outer cannula and spaced from the distal tip of the outer cannula.

Figure 9:
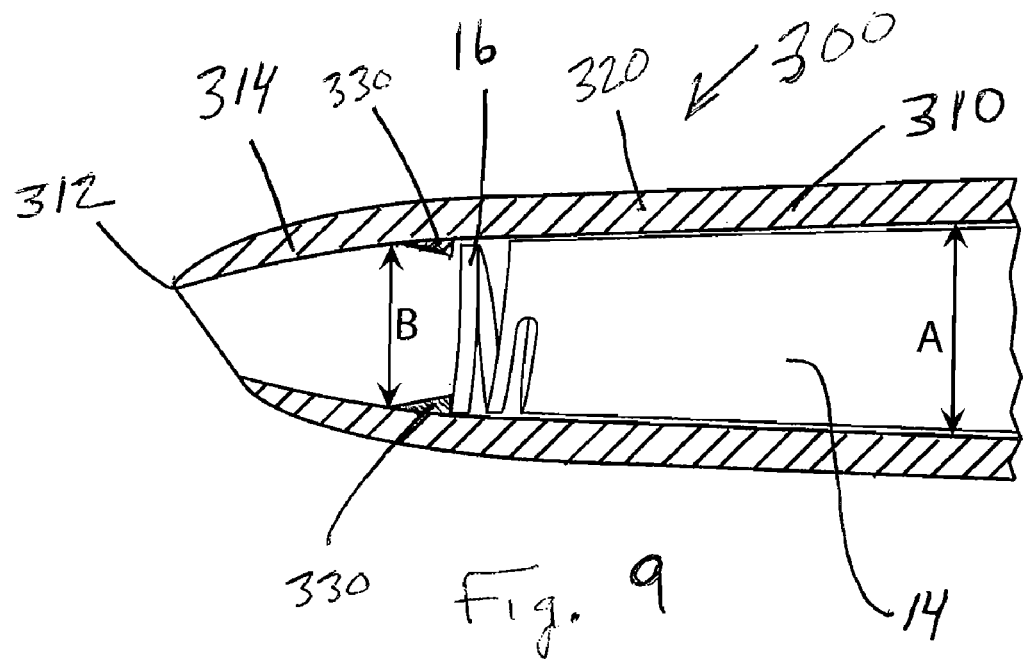
FIG. 9 is a cross-sectional view of a biopsy needle according to yet another embodiment.

Now referring to FIG. 9, a biopsy needle 300 is illustrated and includes an outer cannula 310 and inner tube 14 with snare 16. Unlike the outer cannula 12, the outer cannula 310 does not include a distinct internal shoulder between two sections of different diameters. Instead, an inner surface of the outer cannula 12 has a tapered construction toward the distal end 312 thereof. However, there is a distal end section 314 that has a reduced diameter (less than or equal to B) and a section 320 that has a diameter that is great enough to accommodate the inner tube 14 and snare 16.

Along the inner surface of the outer cannula 310 near or at the interface between sections 314 and 320, a land or platform 330 is provided. The land or platform 330 can be a single tab, two or more discontinuous tabs or an annular ring that extends circumferentially around the inner surface of the outer cannula 310. The land 330 serves a number of different purposes including that the land 330 provides an attachment surface for coupling the snare 16 and therefore, the inner tube 14, to the outer cannula 310. Any number of different means can be used to securely attach the snare 16 to the land 330. For example, a heat weld or the like can be used to attach the two structures. Thus, the land 330 preserves the axial spacing of the snare 16 from the distal end 312, while also providing a welding surface or a surface to establish a mechanical connection.

In this embodiment, the inner tube 14 and snare 16 are inserted into the outer cannula 310 and advanced longitudinally until the snare 16 encounters the land 330, thereby locating the snare 16 a prescribed, desired distance from the distal end 312. This ensures that the distal end section 314 of reduced diameter is preserved and is located so that the specimen is first received into the section 314 prior to the snare 16. Thus, the land 330 also acts as a spacer in that it locates and spaces the distal end of the snare 16 a predetermined distance from distal end 312 of the outer cannula 310, all while the R-factor requirement is satisfied.

As with the other embodiment, the needle 300 design preserves the R ratio as described above and in particular, the distal end section 314 of the outer cannula 310 and the snare 16 are constructed so that the ratio R is greater than 1, thereby eliminating the occurrence of the obstruction phenomena that makes it difficult for the specimen to move forward into the needle 10 or compromises specimen recovery at the conclusion of the procedure.

It will also be appreciated that other means can be provided for preserving the spacing of the snare 16 from the distal end of the outer cannula by providing a stop member and also provide a surface for attaching the snare 16 to the outer cannula by a mechanical fit or some other type of fit. However, as in the other embodiments, the attachment member serves to maintain the distal end section with reduced diameter. In the embodiment shown in FIG. 9, the land or stop member can have a beveled or ramped surface that directs specimen into the snare 16.

In most embodiments, the snare 16 is an integral part of the inner tube 14. Also, in the embodiment of FIG. 8, the axial tab can be in the form of a coaxial sleeve, as in the '391 patent, that is received in the outer cannula. The sleeve introduces the reduced diameter section B into the needle while maintaining the R-factor requirement.

It will therefore be understood that the R-factor requirement of the present invention offers improved specimen transit since the specimen's travel into the distal tip and then into the snare is one of a smooth, non-obstructed travel. In other words, by having a reduced diameter section and then a larger diameter snare located within the interior of the outer cannula and spaced from the distal tip thereof, the specimen travels from a reduced diameter section (distal tip section) into a greater diameter section (compartment), namely, the interior of the open snare, without encountering an obstruction that can break apart or impede the travel of the specimen into the snare as in the prior art devices. This design results in improved performance and specimen capture due to improved specimen transit into the distal tip and then into the snare.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue from a patient comprising:
    an outer tube having a distal end section that has an inner diameter ($ID_{tip}$);
    an inner tube within said outer tube; and
    a snare having a first proximal end connected to the inner tube and a second distal end coupled to the outer tube and having an inner distal diameter ($ID_{sc}$), wherein the distal end section with inner diameter ($ID_{tip}$) is more distally located relative to the snare when the snare is coupled to the outer tube, wherein said snare has a variable diameter that is controlled by rotation of the inner tube with respect to the outer tube in a prescribed direction resulting in the opening and closing, respectively, of the snare, wherein a ratio $(R)=(ID_{sc})/(ID_{tip})$ is greater than 1; and
    wherein a first axially directed coupling element is located at the distal end of the snare and the outer tube includes a second axially directed coupling element that is complementary to and designed to engage the first axially directed coupling element at the second end of the snare for coupling the snare to the outer tube.

2. The biopsy needle of claim 1, wherein R is greater than 1.15.

3. The biopsy needle of claim 1, wherein R is greater than 1.20.

4. The biopsy needle of claim 1, wherein R is greater than 1.25.

5. The biopsy needle of claim 1, wherein R is greater than 1.30.

6. The biopsy needle of claim 1, wherein R is greater than 1.35.

7. The biopsy needle of claim 1, wherein the outer tube has a first section with a first diameter and a second section located at a distalmost portion that has a second diameter that is less than the first diameter, the second diameter defining the inner diameter ($ID_{tip}$).

8. The biopsy needle of claim 1, wherein the snare has a first position and a second position, wherein in the first position, the snare has a first diameter and in the second position, the snare has a second diameter that is less than the first diameter, the snare being moved from the first position to the second position by rotation of the inner tube with respect to the outer tube in one direction and being moved from the second position to the first position by rotation in an opposite direction.

9. The biopsy needle of claim 1, wherein the snare is integral with the inner tube.

10. The biopsy needle of claim 1, wherein the snare comprises a helical coil.

11. The needle of claim 1, wherein the first axially directed coupling element is one of a projection and notch and the second axially directed coupling element is the other of the projection and notch.

12. The needle of claim 1, wherein the outer tube has a first section with a first diameter and a second section located at a distalmost portion that has a second diameter that is less than the first diameter, the second diameter defining the inner diameter ($ID_{tip}$) and wherein the second axially directed coupling member is formed along an inner surface of the outer tube at a location where the first section of the outer tube transitions to the second section.

13. A biopsy needle for removal of tissue from a patient comprising:
an outer tube having a distal end that has an inner diameter ($ID_{tip}$);
an inner tube within said outer tube; and
a snare formed as an integral part of the inner tube near a distal end of the inner tube but offset and spaced from the distal end of the inner tube so as to define a distal end section of the inner tube between the snare and the distal end, the distal end section being coupled to the outer tube at a location that is offset from the distal end of the outer cannula and is located more proximate than the distal end of the outer cannula and wherein the distal end section has an inner distal diameter ($ID_{int}$), wherein said snare has a variable diameter that is controlled by rotation of the inner tube with respect to the outer tube in a prescribed direction resulting in the opening and closing, respectively, of the snare, wherein a ratio $(R)=(ID_{int})/(ID_{tip})$ is greater than 1 and a specimen travel path from the distal end, through the distal end section and into the snare is an obstruction free travel path, thereby optimizing specimen collection and wherein a first axially directed coupling element is located at the distal end section and the outer tube includes a second axially directed coupling element that is complementary to and designed to engage the first axially directed coupling element at the distal end section for coupling the snare to the outer tube.

14. A biopsy needle for removal of tissue from a patient comprising:
an outer tube having a distal end section that has an inner diameter ($ID_{tip}$), wherein an inner surface of the outer tube comprises:
a land coupled to an interior of the outer tube;
an inner tube within said outer tube; and
a snare having a first proximal end connected to the inner tube and a second distal end attached to the land of the outer tube and having an inner distal diameter ($ID_{sc}$), the distal end section with inner diameter ($ID_{tip}$) being more distally located relative to the snare when the snare is coupled to the outer tube, wherein said snare has a variable diameter that is controlled by rotation of the inner tube with respect to the outer tube in a prescribed direction resulting in the opening and closing, respectively, of the snare, wherein a ratio $(R)=(ID_{sc})/(ID_{tip})$ is greater than 1, wherein the land is spaced a predetermined distance from the distal end of the outer tube and restricts axial movement of the snare within the outer cannula so as to space the snare a predetermined distance from the distal end and preserves the distal end section having inner diameter ($ID_{tip}$).

15. The needle of claim 14, wherein the land comprises an annular ring on which the snare is seated and is mechanically attached thereto.

16. The needle of claim 15, wherein the snare is attached to the annular ring by a heat weld.

17. The needle of claim 14, wherein the land comprises a plurality of discretely spaced discontinuous tabs.

18. The needle of claim 14, wherein the second distal end is attached to the land of the outer tube by a heat weld.

* * * * *